United States Patent
Maleedy

(10) Patent No.: US 10,588,845 B2
(45) Date of Patent: Mar. 17, 2020

(54) BUBBLE BATH PRODUCTS IN SHAPED GEL FORM

(71) Applicant: BUBBLE LABORATORIES LIMITED, London (GB)

(72) Inventor: Anthony T. Maleedy, Compton Dando (GB)

(73) Assignee: Bubble Laboratiories Limited, London (GB)

( * ) Notice: Subject to any disclaimer, the term of this patent is extended or adjusted under 35 U.S.C. 154(b) by 0 days.

(21) Appl. No.: 15/773,955

(22) PCT Filed: Sep. 28, 2016

(86) PCT No.: PCT/GB2016/053011
§ 371 (c)(1),
(2) Date: May 4, 2018

(87) PCT Pub. No.: WO2017/077266
PCT Pub. Date: May 11, 2017

(65) Prior Publication Data
US 2018/0318201 A1    Nov. 8, 2018

(30) Foreign Application Priority Data
Nov. 6, 2015 (GB) .................................. 1519646.2

(51) Int. Cl.
| | | |
|---|---|---|
| *A61K 8/65* | (2006.01) |
| *A61K 8/42* | (2006.01) |
| *A61K 8/46* | (2006.01) |
| *A61K 8/73* | (2006.01) |
| *A61Q 19/10* | (2006.01) |
| *A61K 8/02* | (2006.01) |
| *A61K 8/04* | (2006.01) |

(52) U.S. Cl.
CPC .................. *A61K 8/65* (2013.01); *A61K 8/02* (2013.01); *A61K 8/0216* (2013.01); *A61K 8/046* (2013.01); *A61K 8/42* (2013.01); *A61K 8/463* (2013.01); *A61K 8/73* (2013.01); *A61Q 19/10* (2013.01)

(58) Field of Classification Search
CPC . A61K 8/65; A61K 8/02; A61K 8/046; A61K 8/0216; A61K 8/73; A61K 8/463; A61K 8/42; A61Q 19/10
See application file for complete search history.

(56) References Cited

U.S. PATENT DOCUMENTS

| | | | | |
|---|---|---|---|---|
| 2003/0114520 A1* | 6/2003 | Pereira | ................. | A61K 8/0208 514/532 |
| 2005/0069514 A1* | 3/2005 | Maleedy | ................. | A61K 8/02 424/70.24 |
| 2012/0101135 A1* | 4/2012 | Klug | ...................... | A01N 37/06 514/345 |

FOREIGN PATENT DOCUMENTS

| | | |
|---|---|---|
| EP | 0345885 A2 | 12/1989 |
| WO | 03/066018 A1 | 8/2003 |

OTHER PUBLICATIONS

International Preliminary Report on Patentability issued in PCT/GB2016/0530110, dated May 8, 2018, 6 pages.
International Search Report and Written Opinion issued in PCT/GB2016/053011 dated Dec. 12, 2016, 10 pages.

* cited by examiner

*Primary Examiner* — Hasan S Ahmed
(74) *Attorney, Agent, or Firm* — Sheridan Ross P.C.

(57) ABSTRACT

The present invention relates to toiletry products and more particularly to toiletry products that are manufactured in shaped forms. In particular, the invention relates to a bubble bath product, more particularly to a bubble bath product in shaped form, for example in shaped gel form. Certain embodiments of the present invention relate to formulations of bubble bath products which may be manufactured in shaped forms, for example in shaped gel form. Other embodiments relate to bubble bath products per se for example in shaped gel form. Other embodiments relate to a process for the manufacture of formulations of bubble bath product and of bubble bath products.

15 Claims, No Drawings

BUBBLE BATH PRODUCTS IN SHAPED GEL FORM

FIELD OF THE INVENTION

The present invention relates to toiletry products and more particularly to toiletry products that are manufactured in shaped forms. In particular, the invention relates to a bubble bath product, more particularly to a bubble bath product in shaped form, for example in shaped gel form. Certain embodiments of the present invention relate to formulations of bubble bath products which may be manufactured in shaped forms, for example in shaped gel form. Other embodiments relate to bubble bath products per se for example in shaped gel form. Other embodiments relate to a process for the manufacture of formulations of bubble bath product and of bubble bath products.

BACKGROUND TO THE INVENTION

Bubble bath products often take the form of liquid, powders or crystals that are added to water to generate foam. However, bubble bath products in shaped forms are also known. WO 03/066018 discloses gelatin based and gelatin encapsulated toiletry products. In particular, the products disclosed therein are bubble bath products in a tablet gel form comprising a surfactant, gelatin and a non-formaldehyde preservative wherein the product is substantially free from formaldehyde.

An important characteristic of bubble bath products in solid forms, such as gels, is that they melt in water at bath temperature to release surfactant to provide the desired bubble foam phenomenon for the user. The temperature at which such products melt is thus critical to the ability of the products to produce a bubble bath.

The ideal temperature for bath water is dependent on the user and their preferences, but a comfortable temperature is usually considered to be at or above body temperature, for example between 35° C. and 45° C., for example between 37° C. and 41° C. In particular, for infants and children, it is recommended by healthcare professionals that the temperature of bath water should be between 37° C. and 38° C.

It is therefore important that the bubble bath product melt at a temperature that is at or less than the temperature of the bath water to which it is to be added, preferably at a temperature of 37° C. or less, preferably at a temperature of 36° C. or less, for example 35° C. or less, for example 34° C. or less. It is also advantageous if the bubble bath product melts relatively quickly to generate the foam.

However, it is also important that the melting temperature is not too low. The product should retain its desired shape and consistency during the normal course of storage and handling. If the melting temperature is too low, the product may melt at ambient temperature and could spoil or melt in its packaging before it is added to water with the intention of producing a bubble/foam bath. Consequently, products having too low a melting point are not commercially viable. It has been determined that a melting temperature of 28° C. is too low and that a bubble bath product having a melting temperature of 28° C. or less would be likely to melt in its packaging at ambient temperatures that may occur during the normal course of storage or handling.

It is therefore necessary that such products have a narrow range of melting temperature, high enough so as not to melt at ambient temperature but low enough so that the product melts effectively when added to water at optimal bath water temperature. In practice, it would be advantageous if the product has a melting temperature of from 34° C. to 38° C., preferably 35° C. to 38° C.

WO 03/066018 discloses a shaped bath gel that dissipated rapidly in water at 40° C. However, it has been found that the melting temperature of this bath gel is in the region of 27° C. to 28° C. It would therefore be advantageous to have a bath gel product with an increased melting temperature.

Surprisingly, it has been found that a bubble bath formulation comprising gelatin and low levels of gellan gum yield bubble bath products having a melting temperature that is higher than that of the bath gel products of the prior art. It has also been found that the presence of gellan gum does not adversely affect the consistency and appearance of the product. Whilst not wishing to be bound by theoretical considerations, it is believed that blending gellan gum with gelatin results in a gel structure having a higher gel strength and a higher setting temperature and melting temperature.

As well as the melting temperature of the product, there are addition product performance requirements that must be considered with regard to producing a commercially viable product. For example, it is important that such products have a pleasing appearance and tactility. It is important that the product is able to maintain this appearance and tactility for an appropriate period of time once it has been removed from its packaging. In this regard it is useful if the product retains moisture content and does not 'dry-out' when exposed to air so as to prevent or minimise product distortion or shrivelling. It is also advantageous if such products have an appropriate shelf life i.e. that they remain effective, useful and suitable for use for a specific period of time. These various different performance requirements can and do give rise to conflict in terms of arriving at a product formulation which is satisfactory. Fortunately, a bubble bath formulation and product is disclosed herein which satisfies one or more of these product performance requirements.

It is an aim of aspects of the present invention to at least partially mitigate the problems associated with the prior art.

It is an aim of certain embodiments of the present invention to provide a bubble bath formulation for use in a bubble bath product in shaped gel form which product has a melting temperature that is greater than 28° C.

It is an aim of certain embodiments of the present invention to provide a bubble bath product in shaped gel form having a melting temperature that is greater than 28° C.

It is an aim of certain embodiments of the present invention to provide a bubble bath formulation for use in a bubble bath product in shaped gel form which product has a pleasing appearance and tactility.

It is an aim of certain embodiments of the present invention to provide a bubble bath product in shaped gel form having a pleasing appearance and tactility.

It is an aim of certain embodiments of the present invention to provide a bubble bath formulation for use in a bubble bath product in shaped gel form which product retains moisture content when exposed to air.

It is an aim of certain embodiments of the present invention to provide a bubble bath product in shaped gel form which product retains moisture content when exposed to air.

It is an aim of certain embodiments of the present invention to provide a bubble bath formulation for use in a bubble bath in shaped gel form which product has an appropriate shelf life.

It is an aim of certain embodiments of the present invention to provide a bubble bath product in shaped gel form having an appropriate shelf life.

EMBODIMENTS OF THE INVENTION

In one aspect, the present invention provides a formulation for a bubble bath product comprising surfactant, gelatin and gellan gum wherein the gellan gum is present in a quantity of 0.01 to 0.08% by weight.

In one aspect, the present invention provides a formulation for a bubble bath product comprising water, surfactant, gelatin and gellan gum wherein the gellan gum is present in a quantity of 0.01 to 0.08% by weight.

In one aspect, the present invention provides a bubble bath product in shaped gel form comprising surfactant, gelatin and gellan gum wherein the gellan gum is present in a quantity of 0.01 to 0.08% by weight.

In one aspect, the present invention provides a bubble bath product in shaped gel form comprising water, surfactant, gelatin and gellan gum wherein the gellan gum is present in a quantity of 0.01 to 0.08% by weight.

In one aspect, the present invention provides a process for the preparation of a formulation for a bubble bath product of the invention comprising the steps of:
 i) dissolving gelatin and gellan gum in water at a temperature of 85° C. or more;
 ii) adding surfactant and any other ingredients to the gelatin/gellan gum solution; and optionally
 iii) forming the solution/mixture into the desired shape(s); and/or
 iv) cooling the solution/mixture to a temperature at which a gel is formed.

The gellan gum is dissolved in water in a quantity of from 0.01 to 0.08% by weight based on the total weight of the formulation.

In one aspect, the present invention provides a process for the preparation of a formulation for a bubble bath product of the invention comprising the steps of:
 i) dissolving gelatin and gellan gum in a surfactant solution at a temperature of 85° C. or more;
 ii) adding any other ingredients to the gelatin/gellan gum solution/mixture; and optionally
 iii) forming the solution/mixture into the desired shape(s); and/or
 iv) cooling the solution/mixture to a temperature at which a gel is formed.

The gellan gum is dissolved in a surfactant solution in a quantity of from 0.01 to 0.08% by weight based on the total weight of the formulation.

In one aspect, the present invention provides a process for the preparation of a bubble bath product in shaped gel form of the invention comprising the steps of:
 i) dissolving gelatin and gellan gum in water at a temperature of 85° C. or more;
 ii) adding surfactant and any other ingredients to the gelatin/gellan gum solution;
 iii) forming the solution/mixture into the desired shape(s); and
 iv) cooling the solution/mixture to a temperature at which a gel is formed.

The gellan gum is dissolved in water in a quantity of from 0.01 to 0.08% by weight based on the total weight of the formulation.

In one aspect, the present invention provides a process for the preparation of a bubble bath product in shaped gel form of the invention comprising the steps of:
 i) dissolving gelatin and gellan gum in a surfactant solution at a temperature of 85° C. or more;
 ii) adding any other ingredients to the gelatin/gellan gum solution/mixture;
 iii) forming the solution/mixture into the desired shape(s); and
 iv) cooling the solution/mixture to a temperature at which a gel is formed.

The gellan gum is dissolved in a surfactant solution in a quantity of from 0.01 to 0.08% by weight based on the total weight of the formulation.

Aptly, the surfactant solution in which the gellan gum may be dissolved comprises a quantity of surfactant in range of 10 to 40% by weight, for example 20 to 40% by weight, for example 25 to 35% by weight, for example approximately 30% by weight.

Aptly, the surfactant solution in which the gellan gum may be dissolved comprises a quantity of water in range of 90 to 60% by weight, for example 80 to 60% by weight, for example 75 to 65% by weight, for example approximately 70% by weight.

In one aspect, the present invention provides a formulation obtainable by the process described herein.

In one aspect the present invention provides a bubble bath product in shaped gel form obtainable by the process described herein.

Gellan gum is a naturally occurring polysaccharide that can be derived from the bacterium *Sphingomonas elodea*. It is a water-soluble anionic polysaccharide with a tetrasacchahride repeating unit consisting of two residues of D-glucose and one of each residues of L-rhamnose and D-glucuronic acid. The tetrasacharide repeat has the following structure: $[D\text{-}Glc(\beta 1 \rightarrow 47D\text{-}GlcA(\beta 1 \rightarrow 4)Djhbn\text{-}Glc(\beta 877 \rightarrow u8ir)L\text{-}Rha(\alpha 1 \rightarrow 3)]_n$ and the tetrasacharide units are connected by $(\alpha 1 \rightarrow 3)$ glycosidic bonds.

Gellan gum is available in high acyl and low acyl forms. Low acyl gellan gum products form firm, non-elastic, brittle gels, whereas high acyl gellan gum forms soft, very elastic, non-brittle gels. Varying the ratios of the two forms of gellan produces a wide variety of textures. Gellan gum is commercially available under brands and trademarks such as GELRITE, Nanogel-TC,"Gelrich" Grovgel, AppliedGel or Phytagel. Within the food industry, it is also widely known as a food additive by its E number E418.

Aptly, an embodiment of the invention comprise high acyl gellan gum. Aptly, an embodiment of the invention comprise low acyl gellan gum.

Aptly, an embodiment of the invention provides a formulation, product and/or process comprising gellan gum, for example low acyl gellan gum, in a quantity of at least 0.01, for example at least 0.02, for example at least 0.03% by weight. An embodiment also provides a formulation, product and/or process comprising gellan gum, for example low acyl gellan gum, in a quantity of less than or equal to 0.08, for example less than or equal to 0.07, for example less than or equal to 0.06, for example less than or equal to 0.05% by weight. In particular, an embodiment of the invention provides a formulation, product and/or process comprising gellan gum, for example low acyl gellan gum, in a quantity of 0.01 to 0.07, 0.01 to 0.06, 0.01 to 0.05 and preferably 0.02 to 0.05. More particularly, gellan gum is in a quantity of 0.04 to 0.06% weight. More particularly, gellan gum is in a quantity of 0.05% weight. More particularly gellan gum is low acyl gellan gum in a quantity of 0.05% weight.

Gelatin is an important component of the invention. It is gelatin that allows the product to take on a gel form which is thermo-reversible and to be formed into shaped bubble bath products. Gelatin is a protein and, in common with all proteins, is made up of amino acids joined together by peptide linkages to from polymer chains. It is these polymer chains that give gelatin gels their unique characteristics.

Gelatin is non-toxic and non-irritant to normal skin and eyes and forms stable, elastic gels.

Lime processed gelatins are slightly more stable than acid processed gelatins, particularly in relation to pH values. The shaped gel bubble bath products may have a pH of between 5 and 7. If for any reason the pH is low i.e. less than 5, then the rigidity of the gel decreases. This decrease is significantly sharper with an acid processed gelatin than with a lime processed one.

Although any gelatin may be used in the product according to the invention, it is advantageous to use gelatin that has been manufactured by alkali-treatment of collagen, as gelatins produced by alkali-treatments are in general more pure than gelatins produced by acid treatment of collagen and therefore give rise to stronger more stable gels. It is preferred to use a gelatin having a Bloom strength of not less than 200 g. Gelatins having a Bloom strength in the range 230 to 270 g, preferably 250 g give advantageous results.

The term Bloom strength is used herein in relation to gelatin to indicate the gel strength that is the force (expressed in grammes) required to depress the surface of six 2/3% w/w gel, matured at 10° C. for 16 to 18 hours, a distance of 4 mm using a flat-bottomed plunger 12.7 mm in diameter.

When the gelatin is mixed with hot water it dissolves and, on cooling, the mixture sets as a gel, consisting of continuous aqueous phase and gelatin phases. It is believed that, on setting, a rearrangement of the individual gelatin molecules occurs, giving chain segments that are helical in configuration providing strong but elastic structure. Other substances, for example surfactant molecules, that may be present in the gelatin solution before setting become trapped in the gel structure.

Aptly, an embodiment of the invention provides a formulation, product and/or process wherein the gelatin is present in a quantity of less than or equal to 20% by weight, for example less than or equal to 15% by weight, for example less than or equal to 10% by weight, for example less than or equal to 7% by weight, for example less than or equal to 6% by weight. An embodiment also provides a formulation, product and/or process comprising gelatin in a quantity of at least 2% by weight, for example at least 3% by weight, for example at least 4% by weight, for example at least 5% by weight. In particular, an embodiment of the invention provides a formulation, product and/or process comprising gelatin in a quantity of 2 to 20% by weight, for example 2 to 15% by weight, for example 4 to 15% by weight, for example 4 to 10% by weight, for example 4 to 7% by weight, for example 5 to 7% by weight, for example 5 to 6% by weight. More particularly, gelatin is in a quantity of 5% by weight. More particularly, gelatin is in a quantity of 6% by weight.

For the present invention, it is preferred that the gelatin content is chosen so that the product dissolves rapidly when it comes into contact with warm water in use.

Many cosmetic products make use of other gums. It has been determined that gellan gum, when used alone or in combination with non-gelatin based gums, is not thermo-reversible and therefore not appropriate for use in a gel bubble bath product because the resultant gel does not melt in hot water to produce bubbles. Surprisingly it has been found that an appropriate quantity of gellan gum, when combined with gelatin, is thermo-reversible and does not inhibit the thermo-reversible properties of gelatin thus allowing the product to melt at an appropriate temperature range.

The amount of water, when present, will generally be from 10 to 80% by weight. The actual amount of water to be used should be chosen having regard to the need to form a stable gel having the desired dissolution characteristics in water. For bath and shower gels, it is preferred that the product contain from 1 to 4 parts water per part gelatin.

It will be appreciated that the gel must be sufficiently strong for the product to retain its shape at ambient temperature but that it will dissolve rapidly during normal usage.

Aptly, the relative amounts of the principal components of the gel shaped product (for example gelatin, gellan gum and surfactant) are selected so that the product dissolves in water at bath temperature in not more than 6 minutes, for example not more than 5 minutes, for example not more than 3 minutes. Bath water temperature is for example between 35° C. to 45° C., more particularly between 37° C. to 41° C.

A surfactant of the invention may be anionic, amphoteric or nonionic.

Examples of anionic surfactants include sulfate, sulfonate, and phosphate esters, docusates and carboxylates. A surfactant may be selected from ammonium lauryl sulfate, sodium lauryl sulfate, sodium laureth sulfate and sodium myreth sulfate. A surfactant may be selected from dioctyl sodium sulfosuccinate, perfluorooctanesulfonate (PFOS), perfluorobutanesulfonate and linear alkylbenzene sulfonates (LABs). A surfactant may be selected from sodium stearate, sodium lauroyl sarcosinate and carboxylate-based fluorosurfactants such as perfluorononanoate, perfluorooctanoate (PFOA or PFO).

Examples of amphoteric surfactants include phospholipids phosphatidylserine, phosphatidylethanolamine, phosphatidylcholine, and sphingomyelins.

Examples of nonionic surfactant include fatty alcohols, cetyl alcohol, stearyl alcohol and cetostearyl alcohol (consisting predominantly of cetyl and stearyl alcohols), and oleyl alcohol. A surfactant may be selected from polyoxyethylene glycol alkyl ethers (Brij): $CH_3-(CH_2)_{10-16}-(O-C_2H_4)_{1-25}-OH$, octaethylene glycol monododecyl ether, pentaethylene glycol monododecyl ether, polyoxypropylene glycol alkyl ethers: $CH_3-(CH_2)_{10-16}-(O-C_3H_6)_{1-25}-OH$, glucoside alkyl ethers: $CH_3-(CH_2)_{10-16}-(O\text{-Glucoside})_{1-3}-OH$, decyl glucoside, lauryl glucoside, octyl glucoside, polyoxyethylene glycol octylphenol ethers: $C_8H_{17}-(C_6H_4)-(O-C_2H_4)_{1-25}-OH$, triton X-100, polyoxyethylene glycol alkylphenol ethers: $C_9H_{19}-(C_6H_4)-(O-C_2H_4)_{1-25}-OH$, nonoxynol-9, glycerol alkyl esters (for example glyceryl laurate), polyoxyethylene glycol sorbitan alkyl esters (for example polysorbate), sorbitan alkyl esters, cocamide MEA, cocamide DEA, dodecyldimethylamine oxide, block copolymers of polyethylene glycol and polypropylene glycol: poloxamers, and polyethoxylated tallow amine (POEA).

Aptly the surfactant is selected from disodium laureth sulfosuccinate, sodium $C_{14-16}$ olefin sulfonate, sodium laureth sulfate, and lauramide DEA.

Aptly the surfactant is sodium laureth sulfate (sodium laureth ether sulfate SLES).

Aptly the surfactant, for example sodium laureth sulfate, is present as a surfactant solution at a quantity of from 40 to 60% by weight, for example from 45 to 55% by weight, for example 50% by weight. The surfactant solution may comprise surfactant in the range of 25 to 35% by weight, for example approximately 30% by weight. The surfactant solution may comprise water in the range 65 to 75% by weight, for example approximately 70% by weight.

Aptly the surfactant, for example sodium laureth sulfate, is present as a surfactant solution at a quantity of from 15 to 25% by weight, for example from 18 to 22% by weight, for example approximately 21.5% by weight. The surfactant solution may comprise surfactant in the range of 65 to 75% by weight, for example approximately 70% by weight. The surfactant solution may comprise water in the range 25 to 35% by weight, for example approximately 30% by weight.

Aptly the surfactant, for example sodium laureth sulfate, is present at a quantity of from 12 to 18% by weight, for example from 13.5 to 16.5% by weight, for example approximately 15% by weight.

Aptly the invention comprises a foam booster and stabiliser. Examples include cocamide DEA and PPG-2 hydroxyethyl cocamide. Aptly the invention comprises cocamide DEA.

Cocamide DEA may be described as a surfactant but also acts as a foam booster and stabiliser. Cocamide DEA (cocamide diethanolamide) is a diethanolamide made by reacting the mixture of fatty acids from coconut oil with diethanolamine. It is a viscous liquid and is used as a foaming agent in bath products and in cosmetics as an emulsifying agent. The chemical formula of individual components is $CH_3(CH_2)_nC(=O)N(CH_2CH_2OH)_2$ where n typically ranges from 8 to 18.

Aptly a foam booster, for example cocamide DEA, is present in a quantity of from 0 to 10% by weight, for example from 2.5% to 7.5% by weight, for example 5% by weight.

The presence of a humectant in a product of the invention may be desirable to hinder the loss of moisture. It is believed that the presence of a humectant may contribute towards the pleasing appearance and tactility of products of the invention.

Aptly, an embodiment of the invention provides a formulation, product and/or process comprising a humectant. Aptly, the humectant is selected from polyhydric alcohols, for example glycerine, propylene glycol and PEG-7 glyceryl cocoate. Aptly an embodiment of the invention provides a formulation, product and/or process comprising glycerine.

Aptly, an embodiment of the invention provides a formulation, product and/or process wherein the humectant is present in a quantity of less than or equal to 25% by weight, for example less than or equal to 22% by weight, for example less than or equal to 20% by weight. An embodiment also provides a formulation, product and/or process comprising humectant in a quantity of at least 5% by weight, for example at least 10% by weight, for example at least 20% by weight. In particular, an embodiment of the invention provides a formulation, product and/or process comprising humectant in a quantity of 5 to 25% by weight, for example from 10 to 25% weight, for example from 15 to 25% by weight, for example from 18 to 22% weight. Particularly, a humectant is present in a quantity of 20% by weight. More particularly, a humectant is glycerine and is present at a quantity of from 5 to 25% by weight, for example from 10 to 25% weight, for example 15 to 25% by weight, for example 20% by weight.

The presence of a preservative in a product of the invention may be desirable to enhance the shelf life of the product. An adequate amount of preservative can prevent attack by moulds and bacteria. Bacteria and fungal attack can produce opacity in products that are clear, separation in emulsions and pearlescent products and can cause changes in both perfume and colour systems. Fermentation can also occur causing a complete breakdown of the product potentially rendering the product dangerous.

The preservative must be selected that is suitable for the product and in accordance with the legislative requirements in the country of sale.

Aptly, a formulation, product and/or process of the invention may also comprise a preservative. A perservative may comprise parabens. Aptly, a preservative system may selected from:

Phenonip® (phenoxyethanol, methylparaben, ethylparaben, butylparaben, propylparaben, isobutylparaben) (for example available from Clariant);

Phenochem (phenoxyethanol, methylparaben, ethylparaben, butylparaben, propylparaben);

Benzyl alcohol, salicyclic acid, glycerine and sorbic acid (for example available Adina Cosmetic Ingredients);

Methylchloroisothiazolinone and methylisothiazolinone (for example available from Clariant); and Benzyl alcohol and dehydroacetic acid (for example available from Adina Cosmetic Ingredients).

These preservatives are readily available commercially.

Aptly, a formulation, product and/or process of the invention may also comprise benzyl alcohol and dehydroacetic acid (for example Geogard 221).

Aptly, an embodiment of the invention provides a formulation, product and/or process wherein the preservative is present at a quantity of less than or equal to 2% by weight, for example less than or equal to 1.5% by weight, for example less than or equal to 1% by weight. An embodiment also provides a formulation, product and/or process comprising preservative in a quantity of at least 0.1% by weight, for example at least 0.2% by weight, for example at least 0.5% by weight, for example at least 0.7% by weight, for example at least 1% by weight. In particular, an embodiment of the invention provides a formulation, product and/or process comprising preservative in a quantity of from 0.1 to 2% by weight, for example 0.5 to 2% by weight, for example 0.5 to 1.5% by weight, for example 0.7 to 1.5% by weight, for example 0.8 to 1.2% by weight. More particularly, preservative is present at a quantity of 0.9 to 1% by weight. More particularly, preservative is present at a quantity of 1% by weight. More particularly, preservative is present at a quantity of 0.95% by weight. Aptly the preservative, for example benzyl alcohol and dehydroacetic acid is present at a quantity of 0.95 to 1%.

Aptly, a formulation, product and/or process of the invention may also comprise a substance which is bitter to the taste (a bitter substance), for example denotanium benzoate (also known by trade name Bitrex). The use of a bitter substance discourages ingestion of the product by the user (for example a child).

Aptly, an embodiment of the invention provides a formulation, product and/or process wherein the bitter substance is present at a quantity of less than or equal to 2% by weight, for example less than or equal to 1.5% by weight, for example less than or equal to 1% by weight, for example less than or equal to 0.5% by weight. An embodiment also provides a formulation, product and/or process comprising a bitter substance in a quantity of at least 0.001% by weight, at least 0.005% by weight, at least 0.01% by weight, for example at least 0.02% by weight, for example at least 0.05% by weight, for example at least 0.5% by weight, for example at least 1% by weight. In particular, an embodiment of the invention provides a formulation, product and/or process comprising a bitter substance in a quantity of from 0.001 to 2% by weight, for example 0.01 to 2% by weight, for example 0.01 to 0.5% by weight, for example 0.01 to 0.03% by weight. More particularly, a bitter substance is present at a quantity of 0.001 to 0.02% by weight. More particularly, a bitter substance is present at a quantity of approximately 0.005% by weight. More particularly, a bitter substance is present at a quantity of 0.02% by weight.

Aptly, a formulation, product and/or process of the invention may also comprise fragrance.

Aptly, an embodiment of the invention provides a formulation, product and/or process wherein the fragrance is present at a quantity of from 0.05 to 2% by weight. More particularly, a fragrance is present at a quantity of 0.5 to 1.5% by weight. More particularly, a fragrance is present at a quantity of 0.75 to 1.25% by weight. More particularly, a fragrance is present at a quantity of 0.9 to 1.1% by weight. More particularly, a fragrance is present at a quantity of 1% by weight.

Aptly, a formulation, product and/or process of the invention may also comprise a colour in particular cosmetic synthetic grade or vegetable colourings.

Aptly, a formulation, product and/or process of the invention may also by pH adjusted. For example citric acid may be used. Aptly, the pH of the formulation and/or product is between pH 5 and 7, in particular pH 6.

The formulation, product and/or process of the invention may also include one or more further ingredients selected from:
  oils;
  pigments, for example mica pigments;
  pearling agents;
  UV stabilisers, for example benzophenone-1; and
  emulsifers, for example cetyl stearyl alcohol.

A process for the preparation of a formulation of the invention comprises the steps of:
  i) Dissolving gelatin and gellan gum in water at a high temperature, for example a temperature of 85° C. or more;
  ii) Adding surfactant and any other ingredients to the gelatin/gellan gum solution; and optionally
  iii) Forming the solution/mixture into the desired shapes;
  iv) Cooling the solution/mixture to a temperature at which a gel is formed.

The shaped gel product of the invention may be prepared by a process comprising steps i), ii), iii) and iv) as described above.

In step i), the gelling agent is combined with an amount of water sufficient to form a gel, heating the mixture obtained to a temperature not exceeding 98° C. and preferably to 85° C. or above.

The surfactant and/or other ingredients may be added to mixture before or after this heating step. Aptly, the surfactant is added after the heating step (i.e. after the gelatin and gellan gum have dissolved in water). Adding surfactant after dissolving the gelatin and gellan gum assists with cooling of the mixture.

The mixture is cooled to a temperature of between 40° C. and 45° C. Other ingredients such as fragrance may be added after cooling.

Once a gel has formed and the product has been shaped, the product may then be placed or wrapped in suitable packaging. Preferably the packaging is airtight. If desired, the mixture may be placed in a mould that is suitable for inclusion in the packaging in which the product is to be sold. In that case, after the gel has set, the mould containing the shaped product is preferably packed in a suitable container. It has been found that the use of such a mould, particularly one which encloses the product, is advantageous in that it reduces the occurrence of moisture loss from the product.

In accordance with the invention, the gel may be allowed to set in any desired shape, for example resembling the shape of an animal or another object that might be regarded as appealing by consumers, for example by children.

Aptly, the following definitions are used herein.

It should be noted that where values are provided as '% by weight' or '% wt', these values are based on the total weight of the formulation. These values are calculated from the actual weights of each ingredient of the formulation as they are added to the formulation.

It will be appreciated that the terms 'bubble bath' and 'foam bath' as used herein are interchangeable and are exemplary and non-limiting. The mention of one term does not exclude substitution of the other terms in the described embodiment.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

DETAILED DESCRIPTION OF EMBODIMENTS OF THE INVENTION

Embodiments of the present invention will now be described herein, by way of example only.

EXAMPLES 1, 2 and 3

Cold water (balance) was placed in a mixing receptacle and gelatin powder (% by weight as shown in table 1; lime processed; Bloom strength 250 g) and gellan gum (% by weight as shown in table 1) were added. The mixture was then heated to temperature of 85° C. to allow the gellan gum to melt. Once the gelatin and gellan gum were fully dissolved, the heat was turned off and sodium laureth sulfate solution (30% by weight) and cocamide DEA were added separately to the mixture with stirring. Ingredients F, G and H were then added and stirring continued until the mixture became homogenous and clear apart from air bubbles. Colouring as required and fragrance were added and the formulation allowed to stand until air bubbles had escaped.

The mixture was then placed in moulds and allowed to cool. After cooling, it was found that the mixture had set to form a shaped article which could be removed from the mould.

| | % by weight (unless otherwise stated) | | | | |
|---|---|---|---|---|---|
| | Prior Art[1] | Control | Example 1 | Example 2 | Example 3 |
| A. Water | Balance | Balance | Balance | Balance | Balance |
| B. Gelatin | 5 | 6 | 6 | 6 | 6 |
| C. Gellan gum | 0 | 0 | 0.02 | 0.03 | 0.05 |
| D. Sodium laureth sulfate solution | 60 | 50 | 50 | 50 | 50 |
| E. Cocamide DEA | 5 | 5 | 5 | 5 | 5 |
| F. Glycerine | 10 | 20 | 20 | 20 | 20 |
| G. Denatonium benzoate | 0.2 | 0.02 | 0.02 | 0.02 | 0.02 |
| H. Preservative[2] | 0.3 | 1 | 1 | 1 | 1 |
| I. Fragrance | 0.3 | 1 | 1 | 1 | 1 |
| J. Colour | — | Qs | qs | Qs | Qs |
| K. Citric acid | — | pH 6 | pH 6 | pH 6 | pH 6 |
| Melting temperature | 27-28° C. | 28° C. | 33° C. | 33° C. | 35° C. |

[1] Prior art example: WO 03/066018 example 1
[2] Preservative: Prior art: phenonip (phenoxyethonol, methylparaben, ethylparaben, butylparaben, propylparaben, isobutylparaben) Control and examples: dehydroacetic acid and benzyl alcohol

The invention claimed is:

1. A bubble bath product in shaped gel form comprising:
   12% to 18% by weight sodium laureth sulfate;
   4% to 7% by weight gelatin; and
   0.02% to 0.07% by weight gellan gum;
   wherein the product has a melting temperature greater than 28° C.

2. The product according to claim 1 wherein the gellan gum is present in a quantity of 0.02% to 0.05% by weight.

3. The product according to claim 1 wherein the sodium laureth sulfate is present in a quantity selected from 13.5% to 16.5% by weight and 15% by weight.

4. The product according to claim 1 further comprising cocamide DEA.

5. The product according to claim 4 wherein the cocamide DEA is present in a quantity selected from 0% to 10% by weight, 2.5% to 7.5% by weight and 5% by weight.

6. The product according to claim 1 wherein the gelatin is present in a quantity of 5% to 6% by weight.

7. The product according to claim 4 wherein the sodium laureth sulfate is present in a quantity of 15% by weight, the cocamide DEA is present in a quantity of 5% by weight and the gelatin is present in a quantity of 6% by weight.

8. The product according to claim 1 further comprising a humectant.

9. The product according to claim 8 wherein the humectant is glycerine and is present at a quantity selected from 5% to 25% by weight, 10% to 25% weight and 20% by weight.

10. The product according to claim 1, further comprising a preservative.

11. The product according to claim 10 wherein the preservative comprises dehydroacetic acid and benzyl alcohol and the preservative is present at a quantity selected from 0.5% to 2% by weight, 0.9% to 1% by weight and, 0.95% to 1% by weight.

12. The product according to claim 1 further comprising denatonium benzoate at a quantity selected from 0.001% to 2% by weight, 0.005% to 0.05% by weight, 0.005% to 0.03% by weight and 0.005% to 0.02% by weight.

13. The product according to claim 1 further comprising fragrance, at a quantity of 0.05% to 2% by weight.

14. The product according to claim 1 having a pH selected from 5 to 8 and pH 6.

15. The product according to claim 1 comprising:
   water (balance by weight);
   6% by weight gelatin;
   0.05% by weight gellan;
   15% by weight sodium laureth sulfate;
   5% by weight cocamide DEA;
   20% by weight glycerine;
   0.005% to 0.02% by weight denatonium benzoate;
   1% by weight preservative comprising dehydroacetic acid and benzyl alcohol;
   1% by weight fragrance;
   colour; and
   citric acid (to pH 6).

* * * * *

UNITED STATES PATENT AND TRADEMARK OFFICE
CERTIFICATE OF CORRECTION

PATENT NO. : 10,588,845 B2  
APPLICATION NO. : 15/773955  
DATED : March 17, 2020  
INVENTOR(S) : Anthony T. Maleedy Page 1 of 1

It is certified that error appears in the above-identified patent and that said Letters Patent is hereby corrected as shown below:

In the Claims

Column 12, Claim 15, Line 32, please delete "0.05% by weight gellan" and insert --0.05% by weight gellan gum--

Signed and Sealed this
Tenth Day of August, 2021

Drew Hirshfeld
*Performing the Functions and Duties of the
Under Secretary of Commerce for Intellectual Property and
Director of the United States Patent and Trademark Office*